United States Patent [19]

Pircio et al.

[11] Patent Number: 4,600,578

[45] Date of Patent: Jul. 15, 1986

[54] METHOD OF INHIBITING DIARRHEA

[75] Inventors: Anthony W. Pircio, Manlius; Joseph P. Buyniski, Syracuse, both of N.Y.; William T. Comer, Greenwich, Conn.

[73] Assignee: Bristol-Myers Company, New York, N.Y.

[21] Appl. No.: 609,269

[22] Filed: May 11, 1984

[51] Int. Cl.$^4$ .............................................. A61K 31/74
[52] U.S. Cl. ........................................ 424/78; 424/79
[58] Field of Search .................................. 424/78, 79

[56] References Cited

U.S. PATENT DOCUMENTS

| | | | |
|---|---|---|---|
| 3,158,538 | 11/1964 | Lee | 424/79 |
| 3,202,577 | 8/1965 | Markus | 424/79 |
| 3,234,150 | 2/1966 | Feldt et al. | 260/2.1 |

OTHER PUBLICATIONS

AMA Drug Evaluations 5th Edition, American Medical Association, Chicago, Ill., 1983, pp. 1237, 1238, 1289, 1290, 1240 & 1662.

*Primary Examiner*—Frederick E. Waddell
*Attorney, Agent, or Firm*—Lester E. Johnson

[57] ABSTRACT

Oral administration of particular quaternized vinylimidazole-ethylene glycol dimethacrylate copolymers inhibits diarrhea.

7 Claims, No Drawings

METHOD OF INHIBITING DIARRHEA

TECHNICAL FIELD

This invention relates to using oral administration of particular resins to inhibit diarrhea in mammals.

BACKGROUND OF THE INVENTION

It is known to use sequestering agent resins to bind non-absorbed bile acids in the intestinal tract to form complexes which are excreted in the feces whereby bile acids which would otherwise be reabsorbed and returned to the liver are removed from the system. This interrupts the enterohepatic cycle and leads to increased oxidation of cholesterol to bile acids and reduction in plasma cholesterol level. Such sequestering agent resins have been recognized for use for treatment of hypercholesterolemia especially primary hypercholesterolemia (i.e. elevated low density lipoproteins). Recently, it has been recognized that reducing serum cholesterol has a beneficial effect on protecting against the occurrence of atherosclerosis including heart disease. Thus, sequestering agent resins for bile acids have recently assumed increased importance.

Cholestyramine is one sequestering agent resin currently being used to lower blood cholesterol levels in humans by binding bile acids in the intestinal tract. Since it is orally administered, the fact that it has an undesirable odor and taste requires use in combination with masking excipients. Moreover, while cholestyramine is quite effective in binding bile acids in vitro, binding at between 50 and 80% of its theoretical capacity, in vivo much of the bile acid is stripped off in the ileum so that cholestyramine has a low gram potency. This low gram potency in combination with bulk added by the need for masking excipients has resulted in need for a daily intake of 27-54 grams per day which has inhibited widespread use of the drug.

Colestipol is another resin orally administered to sequester bile acids to reduce blood cholesterol level. It has a potency about 50% of cholestyramine.

Recently sequestering agent resins, including cholestyramine and colestipol, have been considered to protect against or treat diarrhea. Numerous clinical reports during the past 10 years have shown cholestyramine to be beneficial in treatment of certain chronic infantile diarrheas. This alternative is significant because infantile diarrhea leads to water and essential salt loss with the consequent risk of dehydration and the normal treatment of hydration and administration of essential salts sometimes is ineffective. Oral administration of cholestyramine has also been beneficial in instances where diarrhea is considered to be caused by the cathartic effect of bile acids reaching the colon in increased amounts, such as occurs in ileal resection and by-pass. There is also some indication that cholestyramine may be useful in the treatment of bacterial-induced diarrheas by binding bacterial enterotoxins.

SUMMARY OF THE INVENTION

It has been discovered herein that particular quaternized vinylimidazole-ethylene glycol dimethacrylate copolymers are bile acid sequestering resins which are alternatives for cholestyramine and colestipol.

These copolymers contain from about 1% to about 25% of ethylene glycol dimethacrylate moieties. The term ethylene glycol dimethacrylate moieties is used herein to mean the portions of the copolymer structure derived from ethylene glycol dimethacrylate. The percentages of ethylene glycol dimethacrylate copolymer moieties herein are weight percentages of the copolymer based on the ethylene glycol dimethacrylate reacting to form the polymer.

These copolymers (referred to hereinafter as copolymer I) have polyvinylimidazolium moieties having the structural formula

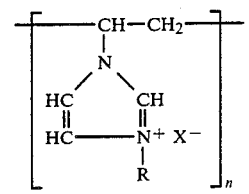

wherein n, on average, ranges from 3 to about 40 and wherein R is selected from the group consisting of alkyl and alkenyl groups having from 1 to 18 carbon atoms and $-CH_2R^1$ wherein $R^1$ is selected from the group consisting of phenyl, $-CH_2OH$, $-CH_2NHCOC_6H_5$, and $-CH_2NR^2R^3$ wherein $R^2$ and $R^3$ are each selected from the group consisting of methyl and ethyl and wherein $X^-$ is an anion. The term "polyvinylimidazolium moiety" is used herein to refer to each portion of the copolymer with the structural formula as depicted above, and n is given on the basis of average values because a plurality of such moieties can be found in a copolymer structure. The average value for n is readily obtained by considering the amount of ethylene glycol dimethacrylate in the copolymer and the number of vinyl groups in the copolymer structure.

Preferred resins referred to hereinafter as copolymers II, which possess about 130 to 160% of the potency of ground cholestyramine in respect to sequestering bile acids in the intestinal tract of rats to form complexes which are excreted in the feces, are the copolymers I which contain from about 15% to about 20% of ethylene glycol dimethacrylate moieties and wherein in the above set forth structural formula n averages from about 3 to about 10 wherein R is alkenyl having from three to four carbon atoms.

As indicated above, the copolymers I and II have utility as sequestrants for bile acids in mammals and are orally administered to said mammals in an amount effective to increase the amount of bile acids in the feces. The copolymers function by binding non-absorbed bile acids in the intestinal tract to form complexes which are excreted in the feces. It is well recognized that removal of bile acids from the intestinal tract in this way lowers blood cholesterol level.

It has been discovered herein that particular of the copolymers I, referred to hereinafter as copolymers III, are useful to inhibit diarrhea in mammals, i.e. as a prophylactic against the occurrence of diarrhea or as treatment for diarrhea. The copolymers III contain from about 1% to about 19% of ethylene glycol dimethacrylate and have polyvinylimidazolium moieties with the above set forth structural formula where n averages from about 25 to about 35 and wherein R is alkyl having from 1 to 3 carbon atoms.

The copolymers III are orally administered in an amount effective to inhibit diarrhea.

DETAILED DESCRIPTION

The copolymers I, II and III herein, as indicated in more detail hereinafter are reaction products wherein one reactant is ethylene glycol dimethacrylate. The ethylene glycol dimethacrylate can be considered a cross-linking agent with potential sites depicted below:

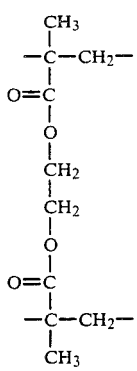

In view of this, the ethylene glycol dimethacrylate (EGD) is sometimes referred to hereinafter as a cross-linking agent.

Turning now to the variables in the resin structure, quaternization is critical because the same resin having structure as that of the invention except that it is unquaternized has very low bile acid binding activity. Furthermore, the selection of R in the copolymer structure set forth above is a variable in respect to bile acid binding activity. Furthermore, it has been found herein that selection of particular R and n in the copolymer structure set forth above and particular percentage EGD cross-linker provides a very high order of bile acid binding activity. Moreover, it has also been found that selection of particular R and n and of ethylene glycol dimethacrylate in place of other reactant/consituent and of the percentage thereof determines anti-diarrheal activity.

So far as $X^-$ is concerned in the above structural formula used in conjuction with describing copolymer I, a wide variety of anions are useful herein, a criterion being the pharmaceutically acceptable nature of such. Suitable anions include, for example, halides, acetate, propionate and phosphate. Chloride is preferred.

As indicated above, the copolymers I have bile acid binding activity. The copolymers II and III herein are species of copolymers I. The copolymers II are very superior bile acid binders and even significantly surpass cholestyramine in this regard. The copolymers III, in addition to having bile acid binding capacity, are excellent anti-diarrheal agents.

Examples of copolymers I which are not copolymers II or III are listed below. These have the structure set forth for copolymers I above and variations in R and n in said structure and the percentage ethylene glycol dimethacrylate moieties (% EGD) are set forth below:

| Copolymer | R | n | % EGD |
|---|---|---|---|
| IA | —CH$_3$ | 5 | 17 |
| IB | —CH$_2$CH$_2$CH$_3$ | 5 | 17 |
| IC | —(CH$_2$)$_7$CH$_3$ | 5 | 17 |
| ID | —(CH$_2$)$_{15}$CH$_3$ | 5 | 17 |
| IE | —CH$_2$C$_6$H$_5$ | 5 | 17 |
| IF | —CH$_2$CH$_2$OH | 5 | 17 |
| IG | —CH$_2$CH$_2$NHCOC$_6$H$_5$ | 4 | 17 |
| IH | —CH$_2$CH$_2$N(C$_2$H$_5$)$_2$ | 4 | 20 |

Examples of copolymer II are listed below. These have structures as set forth for copolymers II above and the variations in R and n in said structures and the percentage ethylene glycol dimethacrylate moieties (% EGD) are set forth below:

| Copolymer | R | n | % EGD |
|---|---|---|---|
| IIA | —CH$_2$CH=CH$_2$ | 5 | 17 |
| IIB | —CH$_2$CH=CH$_2$ | 8 | 16 |
| IIC | —CH$_2$CH$_2$CH=CH$_2$ | 3 | 19 |

Copolymers IIA is preferred for bile acid binding/anti-cholesterol activity.

Examples of copolymers III are listed below. These have structures as set forth for copolymers III above and the variations in R and n in said structures and the percentage ethylene glycol dimethacrylate moities (% EGD) are set forth below:

| Copolymer | R | n | % EGD |
|---|---|---|---|
| IIIA | —CH$_3$ | 30 | 3 |
| IIIB | —CH$_3$ | 25 | 3 |
| IIIC | —CH$_3$ | 35 | 3 |
| IIID | —CH$_3$ | 28 | 7 |
| IIIE | —CH$_2$CH$_3$ | 25 | 9 |
| IIIF | —CH$_2$CH$_2$CH$_3$ | 33 | 2 |

Copolymer IIIA is preferred for anti-diarrheal activity.

In the above, IA-IH, IIA-IIC and IIA-IIIF, the resins have structure as set forth for copolymer I with $X^-$ as chloride. Useful resins are also provided when the $X^-$ in these exemplary resins is another resin anion as indicated above.

The copolymers I (including species copolymers II and III) are readily prepared, for example, by reacting 1-vinylimidazole and ethylene glycol dimethacrylate and then quaternizing. The reaction of 1-vinylimidazole and ethylene glycol dimethacrylate is readily carried out at, for example, 55° C.–80° C., in the presence of benzoyl peroxide catalyst. For copolymers where the ethylene glycol dimethacrylate moiety content is 10% or more a mixture of aqueous sodium sulfate and ethyl acetate is suitable as a reaction medium. Where such content is less than 10%, benzene is suitable as a reaction medium. Quaternization is carried out by refluxing, for example, in ethanol with quaternizing agent. Chloride formation is advantageously carried out by quaternizing with iodide and then exchanging utilizing silver chloride.

For bile acid binding capacity a dosage of 2 to 5 grams three or four times per day is preferred and with the preferred copolymer for this, namely IIA, 2–3 grams three or four times a day.

For anti-diarrheal activity a dosage of copolymer III of 1–2 grams twice a day for adults and 0.5–1 grams twice a day for pediatric diarrhea, is preferred.

The following examples are illustrative of the discoveries herein.

EXAMPLE I

Preparation of Copolymer IIA

A freshly prepared solution of 1-vinylimidazole (400 ml, 4.44 moles), ethylene glycol dimethacrylate (40 ml, 0.21 moles), and benzoyl peroxide (38.0 g, 0.16 moles) in ethyl acetate (400 ml) was added to an aqueous solution of sodium sulfate (2.0, saturated at 60° C.) kept at 60° C. The mixture was stirred well for 16 hours under nitrogen. The resulting beadlets were collected on a filter and washed four times with water. This material was dried two days in a vacuum oven at 80° C. to give 142.4 g consisting essentially of vinylimidazole-ethylene glycol dimethacrylate copolymer containing 17% ethylene glycol dimethacrylate moiety and having structural formula set forth above for copolymer I with n equal to 5 except that the resin was unquaternized. 50 g of the resulting product and a solution of allyl chloride (100 ml) in ethanol (400 ml) were combined and refluxed with stirring for 4 days. The mixture was cooled, collected by filtration on crepe paper, and washed thrice with ethanol. The resulting product was dried 18 hours at 60° C. in a vacuum oven to 62.30 grams of light brown solid consisting essentially of copolymer IIA as defined hereinbefore.

EXAMPLE II

Preparation of Copolymer IIIA

Benzene (500 ml) was heated to reflux under nitrogen in a flask. Benzoyl peroxide (27.2 g) was dissolved in another 500 ml of benzene and to this was added 300 ml of 1-vinylimidazole and ethylene glycol dimethacrylate (3 ml) to form a solution. This solution was added to the refluxing benzene and washed in with 200 more ml of benzene. The resulting mix was stirred under nitrogen with refluxing for 5 hours. After slight cooling and filtering, the resulting mix was dried under vacuum for 16 hours at 60° C. and then dried further under vacuum at 60° C. to yield 147.8 g of a viscous liquid including vinylimidazole-ethylene glycol dimethacrylate containing 3% ethylene glycol dimethacrylate moiety and having structure formula as set forth above for copolymer I with n equal to 30 except that the resin was unquaternized. This liquid was admixed with ethanol (1 l) and iodomethane (90 ml, 1.44 moles), and stirring at room temperature was carried out for 16 hours. The resulting mix was filtered and washed three times with absolute ethanol to provide a light tan powder with a skin on top. The skin was removed and the powder was dried under vacuum at 60° C. for 23 hours to yield 127.1 g of light brown powder. To 123.4 g of this was added 40 ml of iodomethane and 500 ml of absolute ethanol, and this mix was refluxed for 19 hours, cooled, filtered, washed three times with absolute ethanol and dried at 60° C. under vacuum for 44 hours to yield 137.2 g of poly-3-methyl-1-vinylimidazolium iodide resin. Chloride was then exchanged with iodide as follows: Silver nitrate (144.2 g) was dissolved in water. Sodium chloride (50.8 g) was dissolved in water. The solutions were combined. The resulting silver chloride precipitate was filtered and washed. The washed silver chloride precipitate was combined with the 137.2 g of the resin and 1 l of water. The mixture was stirred well and reluxed for 18 hours. The reaction mixture was centrifuged and the solid was washed with water and centrifuged again. The combined supernatants were concentrated under vacuum at approximately 90° C. Then ethanol was added and concentration under vacuum carried out. This was repeated twice more. Then acetone was added and solid was scraped off the sides of the flask, filtered, dried 17 hours at 72° C. under vacuum and sieved through a #9 screen to yield 96.1 g of copolymer IIIA.

EXAMPLE III

Testing for Bile Acid Binding Activity

Compositions tested herein were copolymers IA, IB, IC, ID, IE, IF, IG, IH, IIA and IIIA as described hereinbefore as well as copolymer IVA (the unquaternized precursor of copolymer IA).

The compositions were tested in vitro as well as in vivo.

The in vitro testing consisted of incubating 20 mg amounts of dry resin in 5 ml of 0.15 M NaCl containing 100 μmoles of sodium cholate for 16 hours of continuous shaking at 37° C. After centrifugation, unbound bile salt remaining in the supernatant was measured by the hydroxysteroid dehydrogenase assay. Results are reported in terms of percentage of the activity of cholestryramine beadlets.

The in vivo testing was carried out in rats as follows: Male weanling rats (Wistar strain) were individually housed and fed a basal diet (20.0% casein, 62.55 Amidex, 10.0% corn oil, 4% non-nutritive fiber, 2.45% mineral mixture and 1.0% vitamin mixture) for a 10 day period. On the basis of body weight and the 10-day weight gain, the animals were selected into groups of 10 animals each and fed the basal diet plus the test resins at 0.25 to 1.0% by weight of the diet for a 14-day test period. During the last four days of the test period feces were collected, freeze-dried, ground and analyzed for bile acids by the hydroxysteroid dehydrogenase enzyme method. Results are reported as a percentage of the activity of cholestyramine fed in the diet at the same percentage value as the test resin.

| Test Results for Example III | | |
|---|---|---|
| Copolymer | In Vitro | In Vivo |
| IA MJ 12577 | 93 | 113[2], 126[1] |
| IB MJ 12826 | 97 | 92[1] |
| IC MJ 12976 | 94 | 91[1], 78[2], 88[3] |
| ID MJ 12845 | 75 | 61[1], 49[2] |
| IE MJ 12675 | 102 | 113[4], 137[5] |
| IF MJ 12682 | 107 | 103[5] |
| IG MJ 12814 | 82 | 78[1], 80[2] |
| IH MJ 12766 | 139 | 79[1], 76[2] |
| IIA (Lot 1) MJ 12678 | 119, 111 | 110[4], 135[5] |
| IIA (Lot 2) | 117 | 98[1], 116[2], 121[3], 131[4], 143[4], 161[5] |
| IIIA MJ 12650 | 101 | 52[1], 51[2] |
| IVA (reference-unquaternized) | 3 | 19[1] |

Footnotes:
[1] Compared to cholestyramine beadlets at 1% of diet.
[2] Compared to cholestyramine beadlets at 0.5% of diet.
[3] Compared to cholestyramine beadlets at 0.25% of diet.
[4] Compared to ground cholestyramine at 1% of diet.
[5] Compared to ground cholestyramine at 0.5% of diet.

As indicated above, the copolymers herein contain at least about 50% of the activity of cholestyramine and preferred copolymer herein (IIA) is from 98% to 161% as effective as cholestyramine. Note also the data for reference resin IVA which indicates unquaternized copolymer has very low activity.

EXAMPLE IV

Testing for Anti-Diarrhea Activity

Compositions tested herein were the same as tested in Example III.

The compositions were tested in vivo in rats as follows: Male Sprague-Dawley rats (150-290 g) were dosed orally with test material 1 hour before receiving a standard dose of castor oil orally (3 ml/rat). The rats were individually caged and examined for the presence of diarrhea at hourly intervals. Control animals had a 100% incidence of diarrhea 1 hour after castor oil administration.

With a dosage of 100 mg of resin per kilogram of body weight, test results were as follows: Copolymers IA, IB, ID, IE, IF, IH, IIA and IVA did not protect against diarrhea in any rats as of 1 hour after castor oil challenge. Copolymers IC and IG protected 17% of rats against diarrhea as of 1 hour after castor oil challenge but failed to protect any rats two hours after castor oil challenge. On the other hand, copolymer IIIA protected 100% of rats against diarrhea 1 hour after castor oil challenge and 17% of rats even two hours after castor oil challenge.

Copolymer IIIA was tested against cholestyramine and colestipol with results as set forth in the following table:

TABLE

Example IV

| Test Compound | No. of Rats | Dose mg/kg (p.o.) | Percentage of Rats Protected Against Diarrhea | | | | | |
|---|---|---|---|---|---|---|---|---|
| | | | 1 | 2 | 3 | 4 | 5 | 6 Hrs. |
| Copolymer IIIA | 6 | 512 | 100 | 100 | 100 | 100 | 100 | 100 |
| | 12 | 256 | 100 | 100 | 100 | 100 | 58 | 17 |
| | 12 | 128 | 100 | 58 | 50 | 33 | 0 | |
| | 12 | 64 | 67 | 25 | 8 | 8 | 0 | |
| | 12 | 32 | 17 | 8 | 0 | | | |
| | 6 | 16 | 0 | | | | | |
| Cholestyramine | 6 | 512 | 100 | 17 | 0 | | | |
| | 12 | 256 | 67 | 8 | 0 | | | |
| | 12 | 128 | 50 | 0 | | | | |
| | 18 | 64 | 33 | 0 | | | | |
| | 18 | 32 | 28 | 0 | | | | |
| | 12 | 16 | 0 | | | | | |
| Colestipol | 6 | 512 | 83 | 0 | | | | |
| | 6 | 256 | 50 | 0 | | | | |
| | 6 | 128 | 17 | 17 | 17 | 17 | 17 | 17 |
| | 6 | 64 | 33 | 0 | | | | |
| | 6 | 32 | 0 | | | | | |
| | 6 | 16 | 0 | | | | | |

The above results indicate that copolymer IIIA at higher dosages protects up to at least 6 hours, and that it is significantly more potent than either cholestyramine or colestipol.

The data indicates an ED50 for copolymer IIIA of 50.8 (38.5–69.3) compared to ED50's for cholestyramine of 107 (68–194) and for colestipol of 213 (118–530).

While the foregoing describes preferred embodiments, modifications within the scope of the invention will be readily evident to those skilled in the art. For example, the resins herein are readily combined with a pharmaceutically acceptable carrier or excipient. Thus, the scope of the invention is intended to be defined by the claims.

We claim:

1. Method for inhibiting diarrhea in mammals, said method comprising orally administering to said mammals a diarrhea inhibiting effective amount of a quaternized vinylimidazole-ethylene glycol dimethacrylate copolymer consisting of from about 1% to about 19% of ethylene glycol dimethacrylate moieties and polyvinylimidazolium moieties having the structural formula

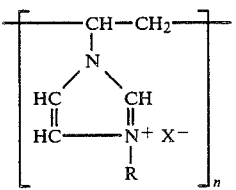

wherein n, on average, ranges from about 25 to about 35, wherein R is alkyl having from 1 to 3 carbon atoms and wherein $X^-$ is a pharmaceutically acceptable anion selected from the group consisting of a halide, acetate, propionate and phosphate.

2. Method as recited in claim 1, wherein the copolymer contains from about 2% to about 5% of ethylene glycol dimethacrylate moieties.

3. Method as recited in claim 2, wherein R in the structural formula is methyl.

4. Method as recited in claim 3, wherein the polyvinylimidazolium moieties have n averaging from about 28 to about 32.

5. Method as recited in claim 4 wherein $X^-$ in the structural formula is halide.

6. Method as recited in claim 5, wherein the polyvinylimidazolium moieties have n averaging about 30.

7. Method as recited in claim 6, wherein $X^-$ in the structural formula is chloride.

* * * * *